United States Patent
Saleh et al.

(10) Patent No.: US 7,232,934 B2
(45) Date of Patent: Jun. 19, 2007

(54) HYDROGENATION OF OXO ALDEHYDES TO OXO ALCOHOLS IN THE PRESENCE OF A NICKEL-MOLYBDENUM CATALYST

(75) Inventors: Ramzi Yanni Saleh, Baton Rouge, LA (US); Stuart L. Soled, Pittstown, NJ (US); Sabato Miseo, Pittstown, NJ (US); Hyung S. Woo, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 363 days.

(21) Appl. No.: 10/938,252

(22) Filed: Sep. 10, 2004

(65) Prior Publication Data

US 2005/0065384 A1 Mar. 24, 2005

Related U.S. Application Data

(60) Provisional application No. 60/504,543, filed on Sep. 19, 2003.

(51) Int. Cl.
C07C 27/00 (2006.01)

(52) U.S. Cl. ..................... 568/876; 568/878; 568/882; 568/883

(58) Field of Classification Search ............ None
See application file for complete search history.

(56) References Cited

U.S. PATENT DOCUMENTS

| | | | |
|---|---|---|---|
| 3,880,940 A | 4/1975 | Baer et al. .................. 260/639 |
| 5,382,715 A | 1/1995 | Vargas et al. ................ 568/882 |
| 5,399,793 A | 3/1995 | Vargas et al. ................ 568/883 |
| 6,278,030 B1 | 8/2001 | Vargas et al. ................ 568/882 |
| 6,355,711 B1 | 3/2002 | Godwin et al. ............. 524/285 |
| 6,482,992 B2 * | 11/2002 | Scholz et al. ................ 568/451 |

OTHER PUBLICATIONS

Journal of Catalysis: vol. 91, pp. 356-360, "Reduced Nickel Hydromolybdate Catalysts: Hydrogen Chemisorption and Activity in Benzene Hydrogenation", 1985.
Applied Catalysis: vol. 10, pp. 63-76 "Morphological, Electronic And Catalytic Properties of Silica-Supported Nickel And Nickel-Molybdenum Catalysts", 1984.

* cited by examiner

*Primary Examiner*—Sikarl A. Witherspoon

(57) ABSTRACT

A reduced or partially reduced nickel-molybdenum catalyst prepared by a process having the steps of 1) reacting nickel carbonate and molybdenum oxide precursors to form nickel molybdate and 2) treating the nickel molybdate under reducing conditions to form the reduced or partially reduced nickel-molybdenum catalyst. There is also a process for making the catalyst. There is also a process for using the catalyst in the hydrogenation of an oxo aldehyde, thereby forming an oxo alcohol of high selectivity. There is also a process for forming an oxo alcohol from the hydroformylation/hydrogenation of an olefinic feedstream. There is also a process for forming an oxo alcohol by contacting formates, dimers, trimers, and organic acids with hydrogen in the presence of a reduced or partially reduced nickel-molybdenum catalyst. The foregoing processes are also useful with a catalyst having the general formula $Y_xZ$ wherein Y is nickel and/or cobalt and Z is molybdenum and/or tungsten; and wherein x ranges between about 0.25 to about 4.0. There are also reduced or partially reduced catalysts of the general formula $Ni_xMo$ or $Y_xZ$ wherein x ranges between about 0.25 to about 4.0 and wherein oxide precursors of the catalysts are substantially free of ammonium groups.

28 Claims, 5 Drawing Sheets

HYDROGENATION OF OXO ALDEHYDES TO OXO ALCOHOLS IN THE PRESENCE OF A NICKEL-MOLYBDENUM CATALYST

CROSS-REFERENCE TO RELATED APPLICATION

This application claims the benefit of U.S. Provisional Application No. 60/504,543, filed Sep. 19, 2003.

BACKGROUND OF THE INVENTION

1. Field of the Invention

The present invention relates to a catalyst useful in hydrogenating oxo aldehydes. The present invention also relates to a process for preparing the catalyst. The present invention further relates to a process for hydrogenating oxo aldehydes.

2. Description of Related Art

Oxo alcohols are employed commercially as plasticizers for polyvinyl chloride plastics. Oxo alcohols are currently prepared by hydroformylating olefins with synthesis gas in the presence of cobalt catalyst to produce oxo aldehydes. The oxo aldehydes are then hydrogenated over a solid catalyst to produce the corresponding alcohols.

Currently, three classes of hydrogenation catalysts are commercially employed. They are the following: sulfided alumina-supported nickel-molybdenum-(sulfided NiMo/$Al_2O_3$); sulfided alumina-supported cobalt-molybdenum-(sulfided CoMo/$Al_2O_3$); and bulk copper chromate (Cu/Cr). The sulfided catalysts are suitable for feedstocks containing or not containing sulfur, whereas the Cu/Cr alloys are effective only with sulfur-free feedstocks. Reaction product alcohol yields range from about 92% to 96% for the sulfided catalysts and about 98% for the Cu/Cr (%=mole percent).

Reduced bulk nickel-molybdenum catalysts have been used in the hydrogenation of benzene. Teachings to such use are described in the Journal of Catalysis, 91, 356–360 (1985), Applied Catalysis, 10, 63–76 (1984). Bulk sulfided nickel-molybdenum and nickel-molybdenum-tungsten catalysts are described in U.S. Pat. Nos. 5,382,715, 5,399,793, and 6,278,030 B1.

It is desirable to have a catalyst system for the hydrogenation of oxo aldehydes that provides higher yields and higher selectivity for oxo alcohols than prior art catalyst systems. It is further desirable to have a catalyst system that converts a higher proportion of by-products (i.e., acids, formates, and trimers) commonly found in oxo aldehyde feedstocks to oxo alcohols.

It was found surprising that there is a catalyst system for hydrogenation of oxo aldehydes that provided high yields and high selectivity for oxo alcohols. It was also found surprising that there is a catalyst system that also converts a significant portion of by-products (i.e., acids, formates, and trimers) commonly found in oxo aldehyde feedstocks to oxo alcohols. It was further yet surprising that there is a catalyst system for hydrogenation of oxo aldehydes that could be incorporated into a hydroformylation process for producing oxo alcohols from olefinic feedstreams. It was still further yet surprising that a non-sulfided alloy catalyst could be used with a sulfur-containing feedstream.

SUMMARY OF THE INVENTION

A reduced or partially reduced nickel-molybdenum catalyst prepared by a process comprising 1) reacting nickel carbonate and molybdenum oxide precursors to form nickel molybdate and 2) treating the nickel molybdate under reducing conditions to form the reduced or partially reduced nickel-molybdenum catalyst.

A process for preparing a reduced or partially reduced nickel-molybdenum catalyst comprises 1) reacting nickel carbonate and molybdenum oxide precursors to form nickel molybdate and 2) treating the nickel molybdate under reducing conditions to form the reduced or partially reduced nickel-molybdenum catalyst.

A process for producing an oxo alcohol that comprises hydrogenating an oxo aldehyde by contacting the oxo aldehyde with hydrogen in the presence of a bulk or supported, reduced or partially reduced nickel-molybdenum catalyst.

Another embodiment includes a process of producing oxo alcohols from the hydroformylation of an olefinic feedstream comprising:

(a) hydroformylating an olefinic feedstream by reaction with carbon monoxide and hydrogen in the presence of a hydroformylation catalyst under reaction conditions that promote the formation of a crude oxo aldehyde product;

(b) demetallating the crude oxo aldehyde product to recover therefrom the hydroformylation catalyst and a substantially catalyst-free, crude oxo aldehyde product;

(c) separating the catalyst-free, crude oxo aldehyde product into a concentrated aldehyde-rich product and an aldehyde-poor product; and (d) hydrogenating the concentrated aldehyde-rich product by contacting the concentrated aldehyde-rich product with hydrogen in the presence of a bulk, i.e., unsupported, or supported, reduced or partially reduced nickel-molybdenum catalyst, thereby forming the oxo alcohol.

The oxo aldehyde is preferably formed from an olefin selected from $C_6$–$C_{20}$ olefins or a mixture of two or more of any of the $C_6$–$C_{20}$ olefins, thereby producing a $C_7$–$C_{21}$ oxo alcohol or a mixture of two or more $C_7$–$C_{20}$ oxo alcohols. The concentrated aldehyde-rich product typically contains above about 30 wt % of aldehyde and the aldehyde-poor product typically contains less than about 30 wt % of aldehyde. The term $C_6$–$C_{20}$ olefins includes any linear or branched $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ and $C_{20}$ olefins and mixtures of two or more thereof. In a preferred embodiment, the olefin is selected from $C_8$, $C_9$, $C_{10}$, $C_{11}$, $C_{12}$ olefins and mixtures thereof, which would provide $C_9$, $C_{10}$, $C_{11}$, $C_{12}$, $C_{13}$ OXO aldehydes and mixtures thereof, respectively.

Preferably, the olefinic feedstream is an olefin selected from $C_6$–$C_{20}$ olefins or a mixture of two or more of any of the $C_6$–$C_{20}$ olefins, such that the resultant oxo alcohol is a $C_7$–$C_{21}$ oxo alcohol or a mixture of two or more of the $C_7$–$C_{21}$ oxo alcohols.

Optionally, the concentrated aldehyde-rich product comprises aldehyde and at least one additional compound selected from the group consisting of: formates, trimers and organic acids. The formates, trimers and organic acids are known impurities produced in such hydroformylation and hydrogenation processes. The formates, trimers, and organic acids are typically present in amount of from about 2 wt % to about 10 wt % based on the weight of the hydroformylation products. The formates are formed from the reaction of the $C_7$–$C_{21}$ oxo alcohols and formic acid. The trimers are aldol condensation products formed from the $C_7$–$C_2$, oxo aldehydes or acetals produced by the reaction of $C_7$–$C_{21}$ oxo aldehyde and $C_7$–$C_{21}$ oxo alcohols. The organic acids are oxidation products formed from the $C_7$–$C_{21}$ oxo aldehydes.

The bulk or supported, reduced or partially reduced nickel-molybdenum catalyst useful in the process of the present invention preferably has the following general formula:

$$Ni_xMo$$

wherein x ranges from about 0.25 to about 4.0, more preferably about 0.5 to about 2.0, and most preferably between about 0.75 to about 1.5.

Another bulk or supported, reduced or partially reduced catalyst useful in the process of the present invention has the following general formula:

$$Y_xZ$$

wherein Y is nickel and/or cobalt and Z is molybdenum and/or tungsten; and wherein x ranges from about 0.25 to about 4.0, preferably about 0.5 to about 2.0; and most preferably between about 0.75 to about 1.5.

Another process according to the present invention for forming an oxo alcohol from formates, trimers and organic acids, which are formed from $C_7$–$C_{21}$ oxo alcohols or oxo aldehydes, comprises hydrogenating an oxygenated organic compound by contacting the oxygenated organic compound with hydrogen in the presence of a catalyst thereby forming the oxo alcohol. The oxygenated organic compound is selected from the group consisting of: formates, trimers and organic acids, which are formed from $C_7$–$C_{21}$ oxo alcohols or oxo aldehydes, and combinations of the foregoing.

One embodiment according to the present invention comprises a reduced or partially reduced nickel-molybdenum catalyst of the general formula:

$$Ni_xMo$$

wherein x is an ranges from about 0.25 to about 4.0. The nickel molybdenum oxide precursor is preferably substantially free of ammonium groups.

Another embodiment according to the present invention comprises a reduced or partially reduced nickel-molybdenum catalyst of the general formula:

$$Ni_xMo$$

wherein x ranges from about 0.25 to about 4.0. The catalyst is formed from a Ni—Mo oxide precursor exhibiting an X-ray diffraction (XRD) spectra substantially as depicted at the top of FIG. 2. The oxide precursor depicted in FIG. 2 is substantially free of ammonium groups.

Still another embodiment according to the present invention comprises a reduced or partially reduced catalyst of the general formula:

$$Y_xZ$$

wherein Y is nickel and/or cobalt, Z is molybdenum and/or tungsten and x ranges from about 0.25 to about 4.0. The oxide precursors are substantially free of ammonium groups.

The present invention still further relates to a process for hydrogenating oxo aldehydes to oxo alcohols with high selectivity, i.e., up to about 99%.

DETAILED DESCRIPTION OF THE PREFERRED EMBODIMENT

Figure 1:
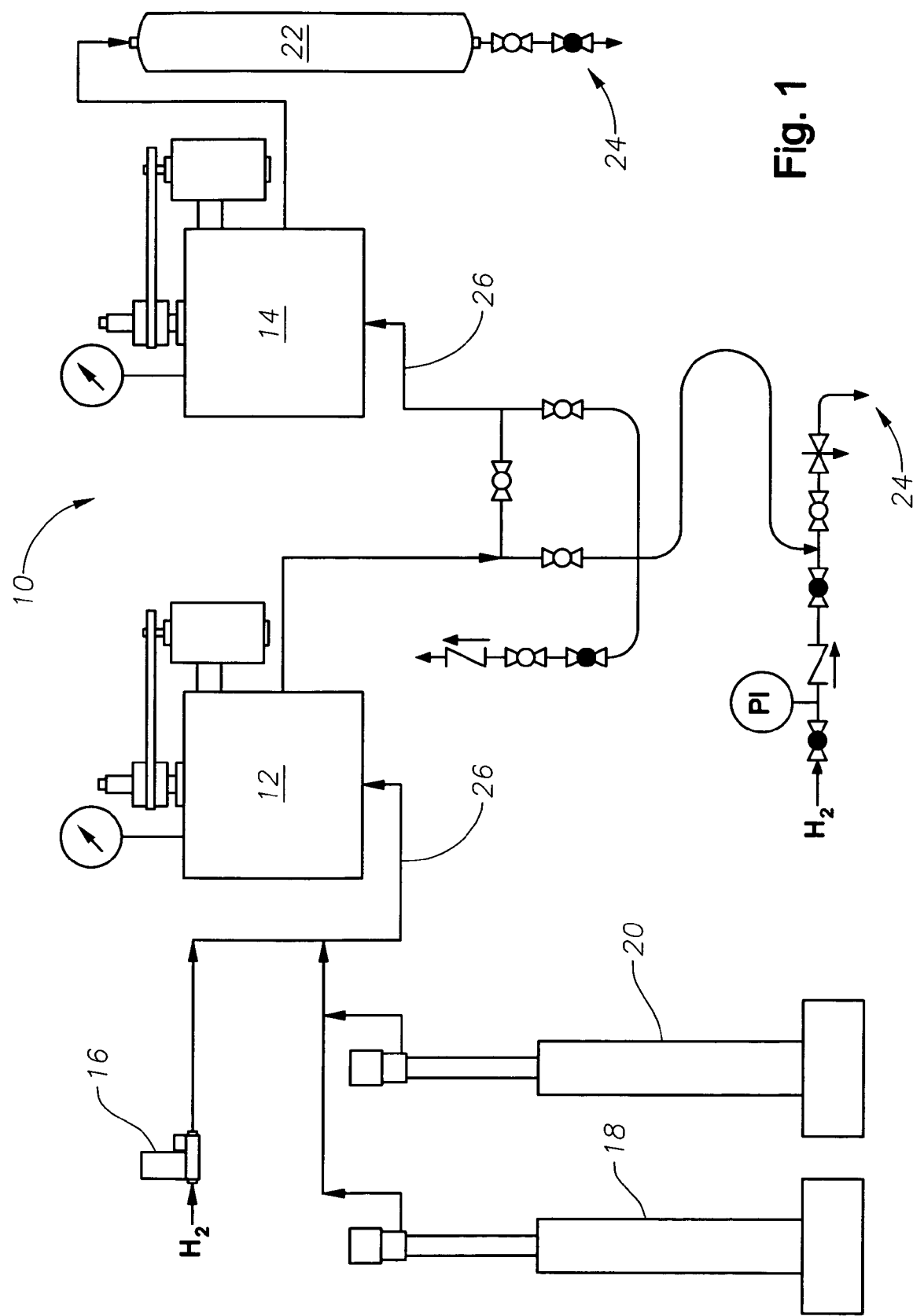
FIG. 1 depicts a simplified schematic view of the continuous autoclave unit employed in the Examples and the Comparative Tests.

In one embodiment according to the present invention, the reduced or partially reduced nickel-molybdenum catalyst is prepared by a process comprising 1) reacting nickel carbonate and molybdenum oxide precursors to form nickel molybdate and 2) treating the nickel molybdate under reducing conditions to form the reduced or partially reduced nickel-molybdenum catalyst. In a preferred process, the catalyst is prepared with ammonium-free mixed metal NiMo oxides.

It is generally desirable to effect a high degree of hydrogenation/reduction of the nickel molybdate when preparing the nickel-molybdenum catalyst. Mixtures of nickel and molybdenum, formed by substantially complete reduction of the oxides, i.e., about at least 99 mole % of the oxides, are properly referred to by the term "alloy" and are encompassed within the meaning of the term "reduced or partially reduced nickel-molybdenum catalyst." The hydrogenation/reduction is typically conducted from about 200° C. to about 750° C. The hydrogenation step typically is conducted from ambient pressure (atmospheric), but may be conducted under superatmospheric pressures, which generally increases the rate of reduction. However, partial reduction is within the scope of the present invention, and such partially reduced catalysts are useful as catalysts in the hydrogenation/hydroformylation processes described below. Partial reduction provides at least about 25 mol % of total Ni content in the reduced or zero valent state, preferably at least about 90 mole % of Ni, and at least about 5 mol % of the total Mo content in the reduced or zero valent state, preferably at least about 50 mol %, based on the total nickel oxide and molybdenum oxide, respectively, in the oxide precursor. Partial reduction occurs, for example, when a precursor, such as $Ni_{1.5}$—$Mo_1O_{4.5}$, has residual molybdenum oxide after it is reduced.

In the one process according to the present invention, an oxo aldehyde is hydrogenated by contacting the oxo aldehyde with hydrogen in the presence of a reduced or partially reduced, bulk (i.e., unsupported) or supported nickel-molybdenum catalyst.

In another process, an oxo aldehyde is hydrogenated by contacting the oxo aldehyde with hydrogen in the presence of a reduced or partially reduced, bulk or supported nickel-molybdenum catalyst corresponding to the following formula:

$$Ni_xMo$$

wherein x ranges from about 0.25 to about 4.0, preferably about 0.5 to about 2.0; and most preferably between about 0.75 to about 1.5.

In another embodiment according to the present invention, an oxo aldehyde can also be hydrogenated by contacting it with hydrogen in the presence of a reduced or partially reduced, bulk or supported catalyst corresponding to the following formula:

$$Y_xZ$$

wherein Y is nickel and/or cobalt and Z is molybdenum and/or tungsten; and wherein x ranges from about 0.25 to about 4.0, preferably about 0.5 to about 2.0; and most preferably between about 0.75 to about 1.5.

In one process according to the present invention selectivity for the oxo alcohol of about 80 mole % or more and preferably up to about 99 mole %. The mol % selectivity for the oxo aldehyde is equal to [moles of alcohol/moles of aldehyde converted] times 100.

Another aspect of the present process is the use of the catalyst systems of the present invention in hydroformylation processes for producing oxo aldehydes from olefin fractions. More particularly, oxo alcohols are produced via the so-called "oxo" process by hydroformylation of $C_6$–$C_{20}$ olefin fractions to a corresponding $C_7$–$C_{21}$ oxo aldehyde product or oxonation product, followed by conversion of the crude oxo aldehyde product to an oxo alcohol as discussed above. The hydrogenation of oxo aldehydes to oxo alcohols has selectivities ranging up to about 99 mole %. Some embodiments of the unique reduced or partially reduced catalyst systems have high selectivity of oxo aldehyde to oxo alcohol. Other embodiments of catalysts according to the present invention have the capacity to convert significant portions of formates, trimers and organic acids, which are formed from $C_7$–$C_{21}$ oxo alcohols or oxo aldehydes, commonly contained within the crude oxo aldehyde product to their corresponding oxo alcohols. Some embodiments according to the present invention have high selectivity of reducing oxo aldehyde to oxo alcohol and conversion of significant portions of formates, trimers and organic acids to their corresponding oxo alcohols.

In order to produce oxo alcohol commercially, the hydroformylation process is adjusted to maximize oxo alcohol formation. This can be accomplished by controlling the temperature, pressure, catalyst concentration, and/or reaction time. Thereafter, the demetallated crude oxo aldehyde product is hydrogenated to convert the oxo aldehydes, formats, trimers and organic acids to their corresponding oxo alcohols.

The production of oxo alcohols from the hydroformylation of an olefinic feedstream preferably comprises:
(a) hydroformylating an olefinic feedstream by reaction with carbon monoxide and hydrogen (i.e., synthesis gas) in the presence of a hydroformylation catalyst under reaction conditions that promote the formation of a crude oxo aldehyde product;
(b) demetallating the crude oxo aldehyde product to recover therefrom the hydroformylation catalyst and a substantially catalyst-free, crude oxo aldehyde product;
(c) separating the catalyst-free, crude oxo aldehyde product into a concentrated aldehyde-rich product and an aldehyde-poor product; and
(d) hydrogenating the concentrated aldehyde-rich product by contacting the concentrated aldehyde-rich product with hydrogen in the presence of a reduced or partially reduced nickel-molybdenum catalyst, thereby forming the oxo alcohol.

The term "substantially catalyst-free" refers to having less than about 50 wt % of the catalyst used in the hydroformylation step present, preferably less than about 10 wt % and more preferably less than about 1 wt % of the catalyst.

Useful hydroformylating catalysts include, but are not limited to, rhodium (Rh), iron (Fe), ruthenium (Ru), iridium (Ir), rhenium (Re), manganese (Mn), osmium (Os), copper (Cu), silver (Ag), gold (Au), palladium (Pd) and platinum (Pt).

The olefinic feedstream is preferably any $C_6$–$C_{20}$ olefin or mixture of two or more of any of the $C_6$–$C_{20}$ olefins. The hydroformylation and subsequent hydrogenation of crude hydroformylation product is capable of producing $C_7$–$C_2$, alcohols, more preferably a $C_9$ oxo alcohol from a $C_8$ olefin.

The oxo process and the use of oxo alcohols in the production of plasticizers are described in U.S. Pat. No. 6,355,711, which is incorporated herein by reference.

Hydrogenation of the crude oxo aldehyde product is typically carried out at a temperature in the range between about 100° C. to about 230° C., more preferably between about 150° C. to about 200° C. Process pressures typically range from between about 500 psig to about 4000 psig and more preferably between about 800 to about 3000 psig.

One embodiment according to the present invention is a process useful for hydrogenating other organic species that are present in the crude aldehyde feedstock, such as formate esters, organic acids, dimers, and trimers. For instance, a feedstock of nonanal (i.e., linear $C_9$ olefin) may have minor proportions of $C_9$ organic acids, formate esters of $C_9$ oxo alcohols, and dimers and trimers of $C_9$ oxo aldehydes and $C_9$ oxo alcohols.

In another process according to the present invention, the catalyst can be used in the bulk form or it can be supported on a suitable support, such as $Al_2O_3$, silica, $SiO_2$—$Al_2O_3$, $TiO_2$, $ZrO_2$, $TiO_2$—$SiO_2$, $TiO_2$—$ZrO_2$, $MgO$—$Al_2O_3$, $MgAl_2O_4$, zeolites, carbon, mesoporous materials (MCM-type) and combinations of the foregoing.

Reduced or partially reduced nickel-molybdenum catalysts useful in the process of the present invention may alternately be prepared by processes described in the Journal of Catalysis, 91, 356–360 (1985) and Applied Catalysis, 10, 63–76 (1984), which are incorporated herein by reference.

The following examples are non-limiting with respect to the present invention. Unless otherwise indicated, all parts or percentages in the Examples are on a weight basis.

EXAMPLES

One reduced nickel-molybdenum (NiMo) catalyst exemplifying the present invention was prepared and tested for hydrogenation efficiency in aldehyde conversion and alcohol selectivity. Catalysts not of the present invention were also prepared and their hydrogenation efficiencies compared to that of catalysts according to the present invention.

The preparations of the exemplified catalysts are set forth in the following paragraphs. The reduced NiMo catalyst exemplifies the catalysts of the present invention. The sulfided $Ni_{1.5}$—$Mo_1O_{4.5}$, reduced massive Ni Catalyst, and sulfided $NiMo/Al_2O_3$ are the catalysts not of the present invention.

Figure 2:
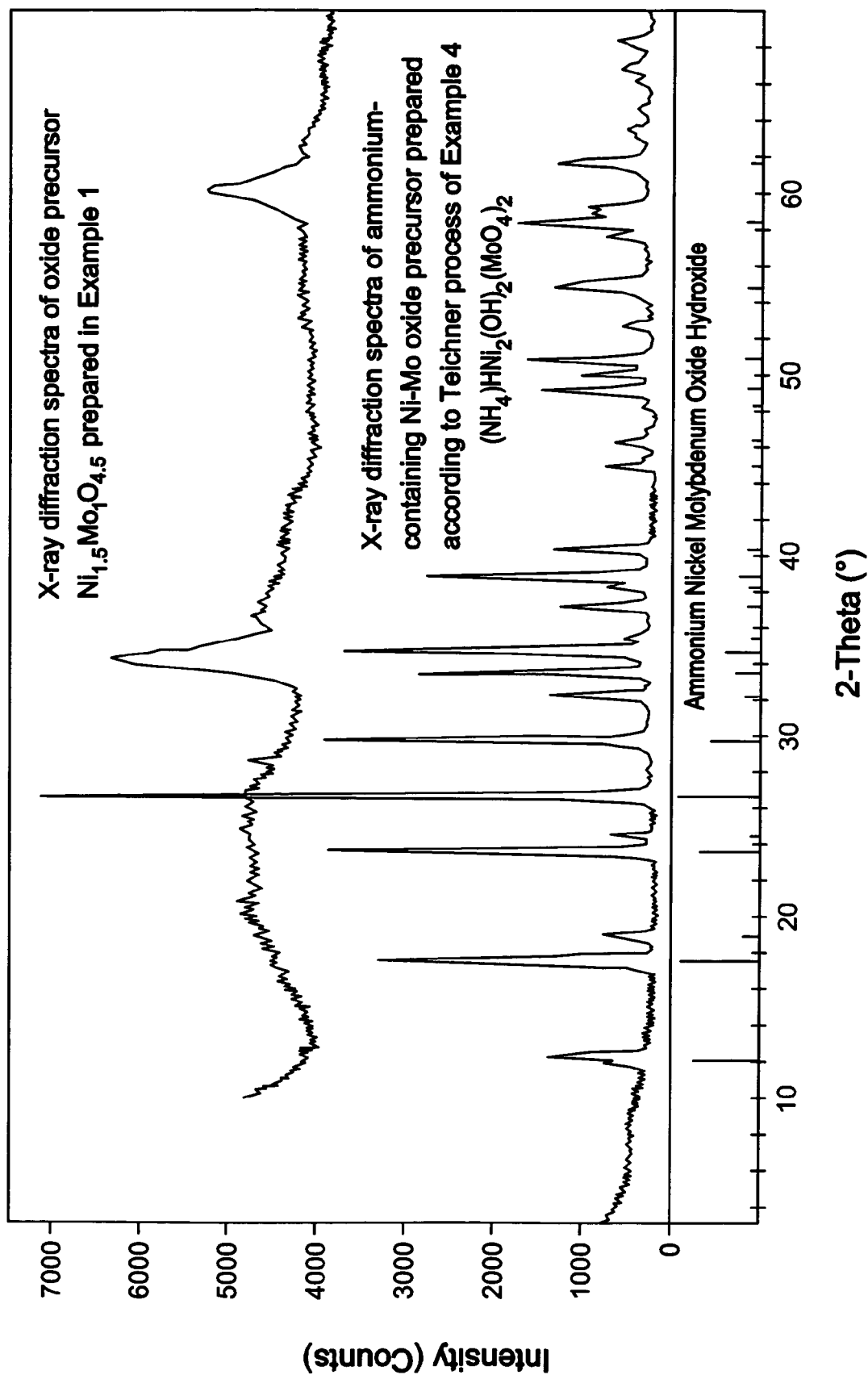
FIG. 2 depicts a XRD spectra of a NiMo oxide precursor of a reduced NiMo catalyst of one embodiment according to the present invention and prepared as described in Example 1 and an ammonium-containing NiMo precursor of a reduced NiMo catalyst prepared by the Teichner process.

Preparation of Reduced One NiMo Catalyst Representative of the Present Invention In a 4 neck round bottom flask equipped with a chilled water condenser and thermometer, 57.6 grams (g) of $MoO_3$ (Formula Weight (F.W.) 143.94 g/mole corresponding to 0.4 mole Mo) were slurried in 800 cubic centimeters (cc) of water along with 0.6 moles of Ni in the form of 70.6 g nickel carbonate—$2NiCO_3 3Ni(OH)_2 4H_2O$ (F.W.=587.67). The slurry took the form of a suspension of the two solids in water. The suspension was heated to 90° C. for 20 hours. The suspension was then filtered. The filtrate was clear. The solid was dried at 120° C. for 16 hours. The dried, isolated material was ammonium-free nickel molybdate ($Ni_{1.5}$—$Mo_1O_{4.5}$). The x-ray diffraction spectra for the dried, isolated material is shown in the top of FIG. 2. The x-ray-diffraction spectra shown in the top of FIG. 2 are collected with CuK α radiation. The x-ray diffraction spectra shown in the top of FIG. 2 comprise a broad amorphous background feature between 18 and 30 degrees two theta, and tow predominant crystalline peaks: one at two theta of 34.2° (d=2.62 Å) and one at 60.10 Å (d=1.54 Å)

A portion of the dried, isolated material was pilled, crushed and sieved to a size of 14–35 mesh. 14 cc (12.2 g) was loaded into a quartz tube reactor and heated at one atmosphere in a stream of 100% hydrogen ($H_2$) at 200 cc/min (cc/minute) at a temperature rate of 1 degree/minute (deg/min) to 325° C. and held at that temperature for 4 hours. The furnace was shut off and then cooled to room temperature with the same 200 cc/min hydrogen flow. After reaching room temperature, the tube was sealed on both ends and transferred into an oxygen-free drybox. The reduced sample was placed into a jar containing 100 cc $n-C_{12}$ that had been purged with flowing nitrogen (500 cc/min) for several hours.

Preparation of Sulfided $Ni_{1.5}$—$Mo_1O_{4.5}$ (Comparative Example)

A portion of the dried oxide (ammonium free nickel molybdate) prepared above was sulfided instead of reduced. 6 cc (5.2 g) of 14–35 mesh of dried oxide was loaded into a quartz tube reactor and heated in one atmosphere of 10% $H_2S$/90% $H_2$ (hydrogen sulfide/hydrogen by mole at 200 cc/min at a temperature rate of 3 deg/min to 400° C. and held at that temperature for two hours. The furnace was cooled to room temperature with the same $H_2S/H_2$ flow. The tube was sealed on both ends and transferred into an oxygen-free drybox. The reduced sample was placed into ajar containing degassed $n-C_{12}$.

Preparation of Reduced Massive Ni Catalyst (Comparative Example)

A commercially obtained massive Ni extrudate was reduced. The Ni catalyst contained 44 weight % Ni as the oxide in a matrix consisting of alumina. The sample was crushed and sieved to a 14–35 mesh size. It was then reduced and stored in substantially the same manner as described above for the reduced $Ni_{1.5}$—$Mo_1O_{4.5}$ catalyst.

Preparation of Sulfided NiMo/$Al_2O_3$ (Comparative Example)

A sample of a commercially obtained NiMo/$Al_2O_3$ extrudate was sulfided with 10% $H_2S$ in $H_2$ substantially in the manner described in the preparation of the sulfided $Ni_{1.5}$—$Mo_1O_{4.5}$ above. The sulfided catalyst was transferred into inert decane for subsequent testing.

Hydrogenation Procedure

The prepared catalysts were used in a hydrogenation process to measure hydrogenation efficiency. All runs used commercially-obtained crude linear nonanal ($LC_9$) as the feed. In addition to aldehydes, the feed also contains small amounts of $C_9$ acids, formate esters of $C_9$ alcohols, dimers of $C_9$, and trimers of $C_9$. A continuous autoclave unit was employed to carry out the hydrogenation process. The unit consists of two continuous stirred tank reactors (CSTR), which were each equipped with dual liquid (oil and water) and hydrogen feed systems, a Robinson-Mahoney stationary catalyst basket, and a heating mantle. A simplified schematic of the continuous autoclave unit is generally referenced by the numeral 10 and is depicted in FIG. 1. There is a reactor 12 and a reactor 14. There is an inlet and mass flow controller 16 for $H_2$ (hydrogen). There is another inlet 26 for $H_2$. There is a pump 18 for aldehyde and a pump 20 for water. There is an accumulator 22 and a sample port 24 to collect product. A Robinson-Mahoney stationary catalyst basket is situated in each CSTR. Each basket consists of two annular mesh screen tubes—one inside the other with an about 3/16 inch (0.48 cm) gap filled with the catalyst (6 cc total). An impeller is placed inside each smaller size mesh screen tube. The entire catalyst basket sits at the bottom of the reactor and is submersed with the feed during operation. The basket is stationary. As the impeller rotates, the feed penetrates through the catalyst. The liquid is continuously fed through the reactor and the reactor is continuously drained through a dip tube located inside the autoclave to maintain a constant liquid level that is high enough to cover the catalyst basket all the time. The catalyst basket is typically loaded with 6 cc of the catalyst under decane. The basket is then placed inside the reactor, the reactor sealed, and the run started. Run conditions are listed in Table 1 below.

TABLE 1

| Item | Description |
|---|---|
| (Run Conditions) | |
| Catalyst volume | 6 ml (cc) |
| Total pressure | 1000 psig, pure $H_2$ |
| Temperatures | 100° C., 125° C., 140° C., 150° C., 160° C., 171° C., 182° C., 192° C. |
| Liquid feed rate | 72 cc/hr |
| $H_2$ feed rate | 245 cc/hr |
| Water | 3% on feed (based on aldehyde) |

A sample of the feed was analyzed prior to exposure to the catalyst. After the unit lined out (equilibrated) at a preset temperature, a sample of the reactor effluent was collected and analyzed by gas chromatography.

Example 1 and Comparative Examples 1 to 3

The catalysts prepared as set forth above were tested for aldehyde conversion and selectivity to the alcohol. Aldehyde conversion and selectivity to the alcohol were calculated according to the following:

wt % Aldehyde converted=[(Aldehyde in feed−Aldehyde in product)/Aldehyde in feed]×100 wt % Selectivity to Alcohol=[(Alcohol in product/Aldehyde converted]×100

TABLE 2

Figure 3:
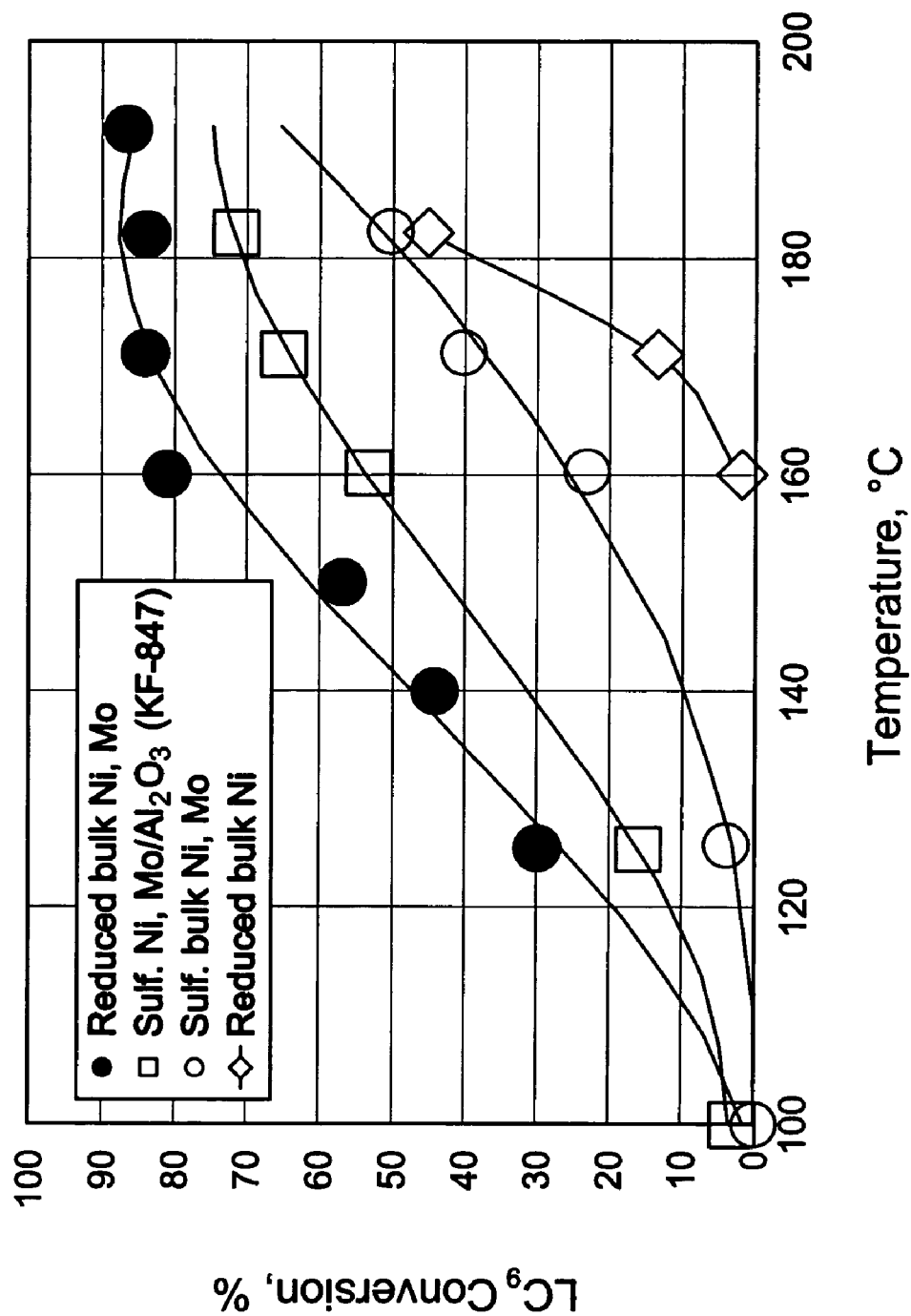
FIG. 3 depicts a plot showing wt % aldehyde converted versus reaction temperature for Example 1 and the Comparative Tests.

LC9 Conversion, % versus Temperature Data for FIG. 3

| Catalyst | Temperature, C. | | | | | | | |
|---|---|---|---|---|---|---|---|---|
| | 100 | 125.5 | 140 | 150 | 160 | 171.1 | 182 | 190 |
| Reduced Bulk Ni—Mo | 1 | 30.1 | 37.9 | 51 | 80.6 | 83.6 | 84 | 86 |
| Sulfided Ni—Mo/Al2O3 | 3.3 | 16.2 | ** | ** | 53.3 | 64.8 | 71 | ** |
| Sulfided Bulk Ni—Mo | 4.9 | 9.8 | ** | ** | 52.6 | 56.9 | 73 | ** |
| Reduced Bulk Ni | ** | ** | ** | ** | 1.9 | 13.4 | 45 | ** |

** Not measured

TABLE 3

Figure 4:
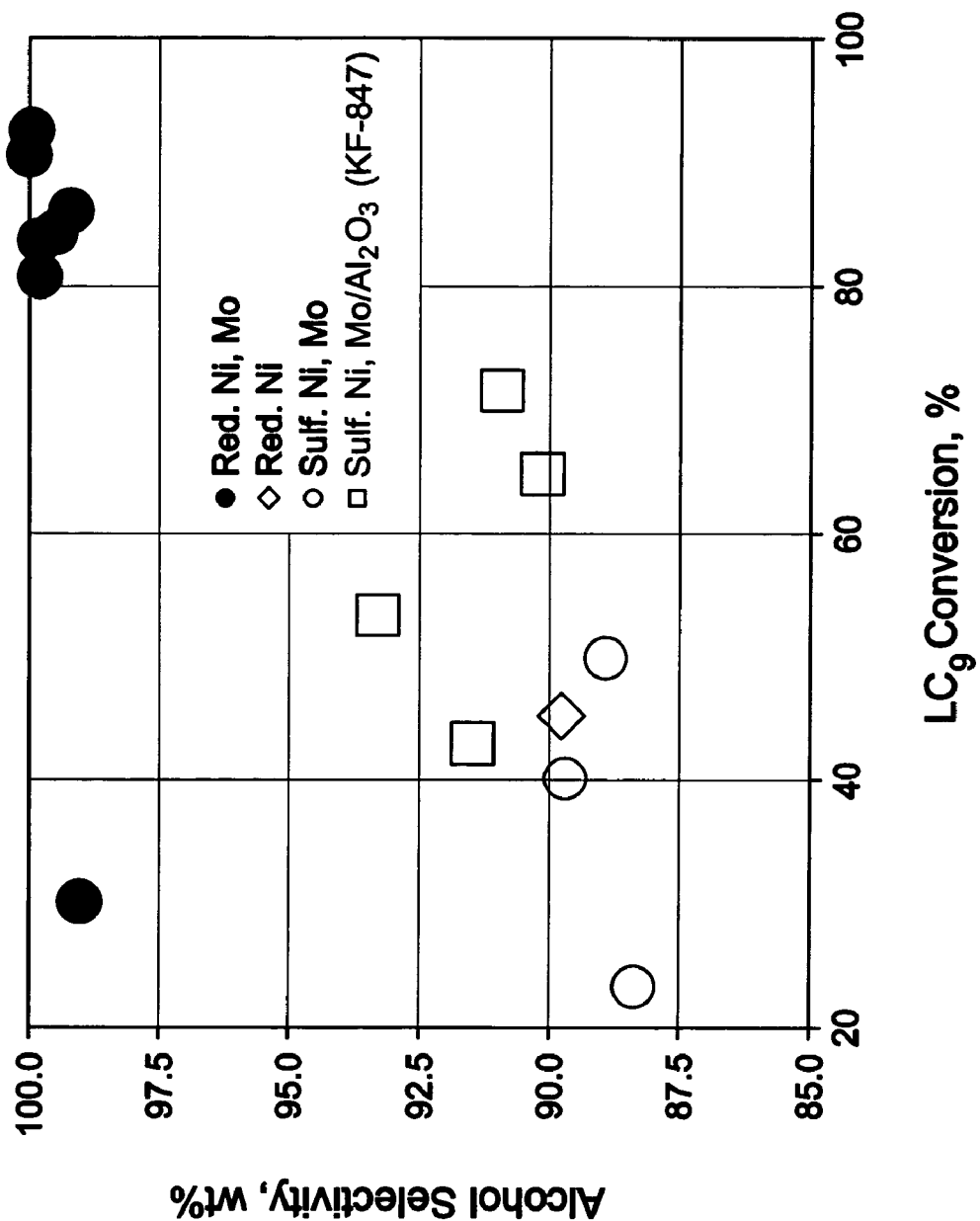
FIG. 4 depicts a plot showing wt % selectivity to the alcohol versus wt % aldehyde conversion for Example 1 and the Comparative Tests.

Alcohol Selectivity, wt % versus LC9 Conversion, % - Data for FIG. 4

| Catalyst | Aldehyde Conversion, % | | | | | | | | | | | | | | | |
|---|---|---|---|---|---|---|---|---|---|---|---|---|---|---|---|---|
| | 19.3 | 23.2 | 30.1 | 40.0 | 43.0 | 45.1 | 49.8 | 53.3 | 64.8 | 71.6 | 80.6 | 83.6 | 84.2 | 86.0 | 90.6 | 92.3 |
| Reduced Bulk Ni—Mo | 99.1 | ** | 99.0 | ** | ** | ** | ** | ** | ** | ** | 99.8 | 99.8 | 99.5 | 99.2 | 100.0 | 100.0 |
| Reduced Bulk Ni | ** | ** | ** | ** | ** | 89.8 | ** | ** | ** | ** | ** | ** | ** | ** | ** | ** |
| Sulfided Bulk Ni—Mo | ** | 88.4 | ** | 89.7 | ** | ** | 89.0 | ** | ** | ** | ** | ** | ** | ** | ** | ** |
| Sulfided Ni—Mo/Al2O3 | ** | ** | ** | ** | 91.5 | ** | ** | 93.3 | 90.2 | 90.9 | ** | ** | ** | ** | ** | ** |

** Not measured

FIG. 3 depicts a plot showing % aldehyde converted versus reaction temperature for all catalysts tested. FIG. 4 depicts a plot showing selectivity to the alcohol versus aldehyde conversion, the aldehyde conversion includes conversion of any formates, trimers and organic acids present.

The reduced NiMo catalyst used in Example 1 was clearly superior to the catalysts used in the Comparative Examples 1 to 3 with respect to both aldehyde conversion and selectivity to the alcohol. FIG. 3 shows that the reduced NiMo catalyst provided higher aldehyde conversions at all temperatures tested. FIG. 4 shows that the reduced NiMo catalyst provided high selectivity to the alcohol along a wide range of aldehyde conversion levels.

Example 2

Conversion of Formates, Trimers, Dimers, and Acids in the Aldehyde Feedstock

The linear aldehyde feedstock (LC$_9$) contained minor proportions of dimers, trimers, organic acids, and formate esters. The feed and the reactor effluent were tested for both aldehyde conversion and selectivity to the alcohol. The reaction temperature was 182° C. The results are set forth in Table 4 below.

TABLE 4

By-Products in Feed and Reactor Effluents (% by weight)

| Catalyst | F (Form) | P (Form) | F (Dim) | P (Dim) | F (Trim) | P (Trim) | F (Acids) | P (Acids) |
|---|---|---|---|---|---|---|---|---|
| Red NiMo | 4.1 | 1.5 | 1.7 | 1.7 | 12.6 | 1.8 | 1.4 | 1.1 |
| Red Ni | 3.9 | 3.2 | 1.9 | 4.8 | 11.8 | 3.3 | 1.4 | 1.3 |
| Sulf NiMo | 4.1 | 3 | 1.7 | 3.9 | 12.6 | 4.9 | 1.4 | 3.1 |
| Sulf NiMo/Al$_2$O$_3$ | 4.5 | 1.9 | 1.6 | 3.5 | 2 | 3.5 | 3.1 | 4.1 |

Figure 5:
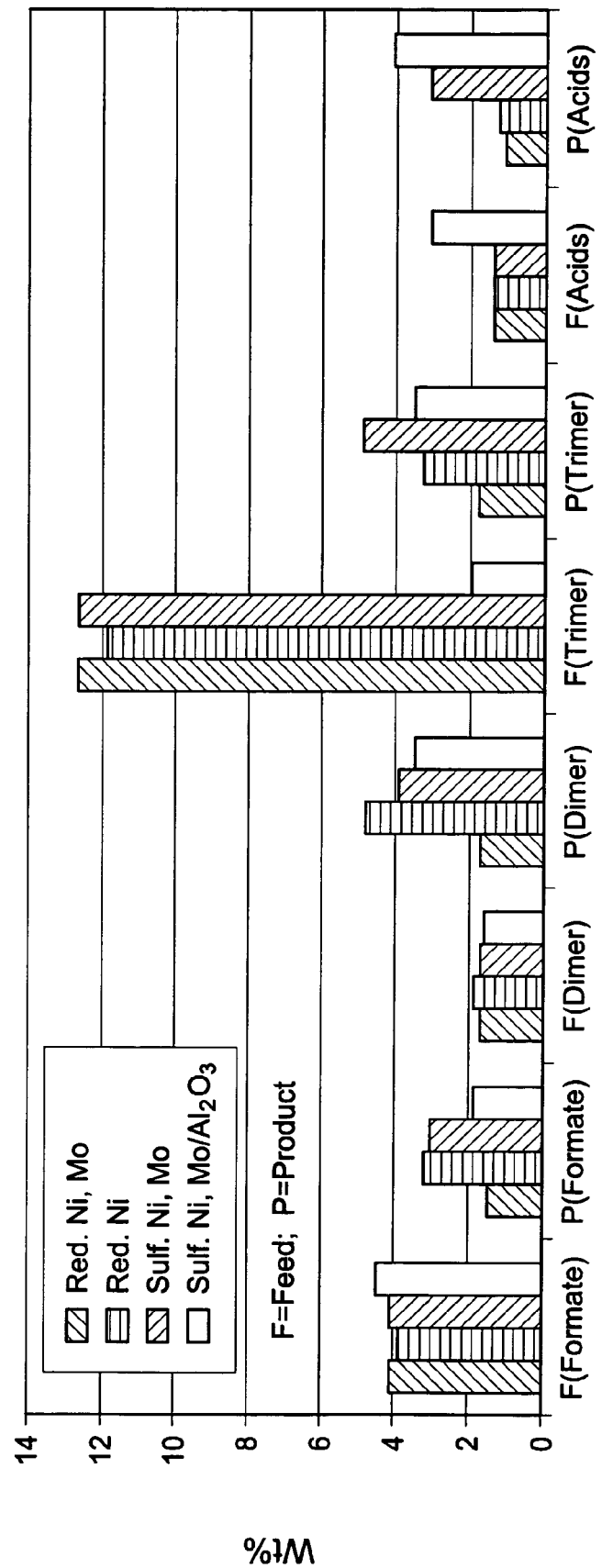
FIG. 5 is a bar graph depicting the data in Table 4.

F = Feed;
P = Reactor effluent;
Form = Formate esters of C$_9$ alcohols; Dim = Dimers of C$_9$ alcohols;
Trim = Trimers C$_9$ of alcohols;
Acids = C$_9$ acids;
sulf = sulfided;
red = reduced FIG. 5 is a bar graph representative of the data set forth above in Table 4.

Table 4 shows that greater amounts of trimers and formates were converted by the reduced NiMo catalyst relative to the other catalysts. Further, the reduced NiMo catalyst did not produce any additional dimers or acids like the other conventional catalysts did.

Resistance of Catalyst to Sulfur

The reduced NiMo catalyst was tested at 180° C. using two linear aldehyde feedstocks (LC$_9$): one feedstock spiked (mixed) with 10 ppm sulfur and the other feedstock with 18 ppm sulfur obtained from di-isopropyl sulfide. Reactor effluent obtained at approximately one-hour intervals on stream using the 10-ppm sulfur feed contained 10 ppm sulfur, and that generated from the 18-ppm sulfur feed also contained 18 ppm sulfur. This indicated that the catalyst did not uptake, i.e., adsorb or react with any sulfur. Furthermore, the catalyst activity or alcohol selectivity did not abruptly change upon addition of the sulfur to the feed. In addition, surface analysis of spent catalyst using x-ray photoelectron spectroscopy indicated no sulfur reaction with the Ni or Mo. These results demonstrate the high tolerance of the catalyst to sulfur.

Comparative Example 4

A reduced nickel-molybdenum catalyst was prepared according to the Teichner process. The method employed incorporates $NH_4$ cations into the catalyst structure.

In a 1 liter flask, 26.5 g ammonium molybdate (0.15 moles Mo) and 43.6 g nickel nitrate hexahydrate (0.15 moles Ni) were dissolved in 300 cc of water so that the resulting pH equaled 4.3. To this solution, a concentrated $NH_4OH$ solution was added. At first, a precipitate formed which on further addition of $NH_4OH$ dissolved to give a clear blue solution with a pH of 8.3, and additional $NH_4OH$ (~250 cc) was added until a pH of 10 was reached. The solution was heated to 90° C. for 3 hours, during which ammonia gas evolved and a green precipitate formed. The final pH was between 6.8 and 7. The suspension was cooled to room temperature, filtered, washed with water and dried at 120° C. overnight. About 18.6 g of material was obtained. The sample analyzed for Ni at 26.6 wt % and Mo at 34 wt %. The XRD spectrum for the catalyst is seen in the top trace in FIG. 2. As is apparent, the pattern is different than that of this catalyst, which is one embodiment according to the present invention (Example 1).

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

We claim:

1. A process for forming an oxo alcohol, the process comprising:
hydrogenating an oxo aldehyde by contacting said oxo aldehyde with hydrogen in the presence of a reduced or partially reduced nickel-molybdenum catalyst, thereby forming said oxo alcohol, wherein said partially reduced nickel-molybdenum catalyst comprises at least about 25 mol % of total Ni content in the reduced or zero valent state and at least about 5 mol % of the total Mo content in the reduced or zero valent state.

2. The process according to claim 1, wherein said reduced or partially reduced nickel-molybdenum catalyst has the general formula:

$Ni_xMo$ wherein x ranges between about 0.25 to about 4.0.

3. The process according to claim 2, wherein x ranges between about 0.5 to about 2.0.

4. The process according to claim 2, wherein x ranges between about 0.75 to about 1.5.

5. The process according to claim 1, wherein a selectivity for said oxo alcohol is about 80 mole % or more.

6. The process according to claim 1, wherein a selectivity for said oxo alcohol is up to about 99 mole %.

7. The process of claim 1, wherein said oxo aldehyde is formed from at least one olefin having from 6 to 20 carbon atoms.

8. The process of claim 1, wherein said oxo alcohol is at least one alcohol having from 7 to 21 carbon atoms.

9. The process according to claim 1, wherein said reduced or partially reduced catalyst is in bulk form.

10. The process according to claim 1, wherein said reduced or partially reduced catalyst is supported.

11. The process according to claim 1, wherein an oxide precursor of the catalyst is substantially free of ammonium and ammonia groups.

12. The process of claim 11, wherein said reduced or partially reduced nickel-molybdenum catalyst is supported by at least one compound selected from the group consisting of $Al_2O_3$, silica, $SiO_2$—$Al_2O_3$, $TiO_2$, $ZrO_2$, $TiO2$—$SiO2$, $TiO_2$—$ZrO_2$, MgO—$Al_2O_3$, $MgAl_2O_4$, zeolites, carbon, mesoporous materials (MCM-type) and combinations thereof.

13. The process of claim 1, wherein said oxo aldehyde comprises at least one additional compound selected from the group consisting of formates, trimers and organic acids.

14. The process of claim 1, wherein said hydrogenation is carried out at a temperature of between about 100° C. to about 250° C.

15. A process of producing oxo alcohols from the hydroformylation of an olefinic feedstream, the process comprising:
(a) hydroformylating said olefinic feedstream by reaction with carbon monoxide and hydrogen in the presence of a hydroformylation catalyst, thereby forming a crude oxo aldehyde product;
(b) demetallating said crude oxo aldehyde product to recover therefrom the hydroformylation catalyst and a substantially catalyst-free, crude oxo aldehyde product;
(c) separating said catalyst-free, crude oxo aldehyde product into a concentrated aldehyde-rich product and an aldehyde-poor product; and
(d) hydrogenating said concentrated aldehyde-rich product by contacting the concentrated aldehyde-rich product with hydrogen in the presence of a catalyst according to claim 1, thereby forming said oxo alcohol.

16. The process according to claim 15, wherein said reduced or partially reduced nickel-molybdenum catalyst has the general formula:

$Ni_xMo$ wherein x ranges between about 0.25 to 4.0.

17. The process according to claim 15, wherein x ranges between about 0.5 to about 2.0.

18. The process according to claim 15, wherein x ranges between about 0.75 to about 1.5.

19. The process of claim 15, wherein said olefinic feedstream comprises an olefin having from 6 to 20 carbon atoms.

20. The process of claim 15, wherein said oxo alcohol has from 7 to 21 carbon atoms.

21. The process according to claim 15, wherein said reduced or partially reduced nickel-molybdenum catalyst is a supported catalyst.

22. The process of claim 21, wherein said support is selected from the group consisting of: $Al_2O_3$, silica, $SiO_2$—$Al_2O_3$, $TiO_2$, $ZrO_2$, $TiO_2$—$SiO_2$, $TiO_2$—$ZrO_2$, MgO—$Al_2O_3$, $MgAl_2O_4$, zeolites, carbon, mesoporous materials (MCM-type) and combinations thereof.

23. The process of claim 15, wherein said concentrated aldehyde-rich product comprises oxo aldehyde and at least one additional compound selected from the group consisting of formates, trimers and organic acids.

24. The process of claim 15, wherein said hydrogenation step (d) is carried out at a temperature of between about 100° C. to about 250° C.

25. The process of claim 15, wherein said hydroformylation catalyst is selected from the group consisting of Co, Rh, Fe, Ru, Ir, Re, Mn, Os, Cu, Ag, Au, Pd and Pt.

26. A process for forming an oxo alcohol, the process comprising:
hydrogenating an oxo aldehyde comprising: by contacting said oxo aldehyde with hydrogen in the presence of a catalyst thereby forming said oxo alcohol, said catalyst being reduced or partially reduced and having the general formula:

$Y_xZ$ wherein Y is nickel and/or cobalt and Z is molybdenum and/or tungsten; and wherein x ranges between about 0.25 to about 4.0, wherein said partially reduced catalyst comprises at least about 25 mol % of total Ni content in the reduced or zero valent state and at least about 5 mol % of the total Mo content in the reduced or zero valent state.

27. A process of producing oxo alcohols from the hydroformylation of an olefinic feedstream, the process comprising:
(a) hydroformylating said olefinic feedstream by reaction with carbon monoxide and hydrogen in the presence of a hydroformylation catalyst, thereby forming a crude oxo aldehyde product;
(b) demetallating said crude oxo aldehyde product to recover therefrom said hydroformylation catalyst and a substantially catalyst-free, crude oxo aldehyde product;
(c) separating said catalyst-free, crude oxo aldehyde product into a concentrated aldehyde-rich product and an aldehyde-poor product; and
(d) hydrogenating said concentrated aldehyde-rich product by contacting said concentrated aldehyde-rich product with hydrogen in the presence of a catalyst, thereby forming said oxo alcohol; wherein said catalyst is reduced or partially reduced and has the general formula:

$Y_xZ$ wherein Y is nickel and/or cobalt and Z is molybdenum and/or tungsten; and wherein x is ranges between about 0.25 to about 4.0, wherein said partially reduced provides a nickel-molybdenum catalyst comprising at least about 25 mol % of total Ni content in the reduced or zero valent state and at least about 5 mol % of the total Mo content in the reduced or zero valent state.

28. A process for forming an oxo alcohol from at least one by-product selected from the group consisting of formates, dimers, trimers and organic acids, the process comprising:
hydrogenating an organic compound selected from the group consisting of: formates, trimers and organic acids and combinations thereof by contacting said organic compound with hydrogen in the presence of a catalyst, thereby forming said oxo alcohol, wherein said catalyst is reduced or partially reduced so that at least about 25 mol % of total Ni content is in the reduced or zero valent state and at least about 5 mol % of the total Mo content is in the reduced or zero valent state and is selected from the group consisting of:
(a) a nickel-molybdenum catalyst;
(b) a catalyst having the general formula $Ni_xMo$ wherein x ranges between about 0.25 to about 4.0; and
(c) a catalyst having the general formula $Y_xZ$ wherein Y is nickel and/or cobalt and Z is molybdenum and/or tungsten; and wherein x ranges between about 0.25 to about 4.0.

* * * * *